(12) United States Patent
Sato et al.

(10) Patent No.: US 11,940,520 B2
(45) Date of Patent: Mar. 26, 2024

(54) MAGNETIC RESONANCE IMAGING DEVICE, IMAGE PROCESSING DEVICE, AND IMAGE PROCESSING METHOD

(71) Applicant: FUJIFILM Healthcare Corporation, Kashiwa (JP)

(72) Inventors: Ryota Sato, Chiba (JP); Suguru Yokosawa, Chiba (JP); Toru Shirai, Chiba (JP); Kazuho Kamba, Chiba (JP); Yoshitaka Sato, Chiba (JP); Masahiro Takizawa, Chiba (JP)

(73) Assignee: FUJIFILM Healthcare Corporation, Chiba (JP)

( * ) Notice: Subject to any disclaimer, the term of this patent is extended or adjusted under 35 U.S.C. 154(b) by 95 days.

(21) Appl. No.: 17/892,495

(22) Filed: Aug. 22, 2022

(65) Prior Publication Data
US 2023/0062864 A1    Mar. 2, 2023

(30) Foreign Application Priority Data
Aug. 27, 2021 (JP) .................. 2021-139158

(51) Int. Cl.
*G01R 33/56* (2006.01)
*A61B 5/055* (2006.01)
(Continued)

(52) U.S. Cl.
CPC ............ *G01R 33/565* (2013.01); *A61B 5/055* (2013.01); *G06T 11/005* (2013.01); *G06T 2207/10088* (2013.01)

(58) Field of Classification Search
CPC ............. G01R 33/565; G01R 33/5608; G01R 33/546; G01R 33/56341; A61B 5/055;
(Continued)

(56) References Cited

U.S. PATENT DOCUMENTS

2007/0198203 A1    8/2007  Kimura
2019/0128991 A1*   5/2019  Shirai ................. G01R 33/56

FOREIGN PATENT DOCUMENTS

JP         2007-244848 A      9/2007

OTHER PUBLICATIONS

S.J. Holdsworth et al., "Diffusion Tensor Imaging (DTI) With Retrospective Motion Correction for Large-Scale Pediatric Imaging", J. Magnetic Reason. Imaging, 36:961-971 (2012).
(Continued)

*Primary Examiner* — G. M. A Hyder
(74) *Attorney, Agent, or Firm* — Paul Teng (57) ABSTRACT

For a complex image to be complexly added, appropriate phase correction is executed by a simple method to prevent occurrence of an artifact in a signal region and to reduce noise in a background region. Two or more types of smoothing processing with different smoothing degrees are executed on a phase image of the complex image to obtain two or more types of smoothed phase images having different smoothing degrees. A weight for each of these smoothed phase images is calculated based on a signal value (SNR) of an intensity image, and addition is performed by a weight for each signal value to obtain a smoothed phase image for correction. After a phase of the complex image is corrected using the smoothed phase image, a phase-corrected complex image is complexly added. As a result, phase correction equivalent to phase correction in which a smoothing degree is weakened in the signal region and a smoothing degree is strengthened in the background region is realized.

17 Claims, 10 Drawing Sheets

(51) Int. Cl.
  *G01R 33/565*  (2006.01)
  *G06T 11/00*  (2006.01)
(58) Field of Classification Search
  CPC .............. A61B 5/7203; G06T 11/005; G06T 2207/10088
  See application file for complete search history.

(56) References Cited

OTHER PUBLICATIONS

Japanese official action dated Jan. 9, 2024 (and English translation thereof) in connection with Japanese Patent Application No. 2021-139158.
Pizzolato, Marco, et al., "Adaptive phase correction of diffusion-weighted images", Neuroimage, vol. 206, 116274 (2020).
Liu, Feihong, et al., "Gaussianization of Diffusion MRI Data Using Spatially Adaptive Filtering", Proc Intl Soc Mag Reson Med, vol. 27, 4609 (2019).

* cited by examiner

MAGNETIC RESONANCE IMAGING DEVICE, IMAGE PROCESSING DEVICE, AND IMAGE PROCESSING METHOD

BACKGROUND OF THE INVENTION

1. Field of the Invention

The present invention relates to a magnetic resonance imaging device, and an image processing device and an image processing method for processing an image obtained by a magnetic resonance imaging device, and particularly relates to a technique of correcting a phase of each of complex images when adding the complex images.

2. Description of the Related Art

In magnetic resonance imaging (MRI), in order to improve a signal-to-noise ratio (SNR), there are many cases where imaging is performed a plurality of times and a plurality of images obtained as a result of the imaging are added. In particular, in imaging such as diffusion weighted imaging (DWI) in which a diffusion degree of water is enhanced, there is a problem that a phase of moving magnetization is changed and a signal is reduced by applying a gradient magnetic field having a large intensity, which is called a motion probing gradient (MPG) pulse, and a technique of improving the SNR by addition is important.

In general, an image obtained by MRI is obtained as a complex image including phase information. Methods of adding complex images to obtain one image include complex addition of adding the complex images as the complex images are, and absolute value addition of adding images after converting the images into absolute values. When phases are aligned among the images, the complex addition is appropriate, and when the phases are not aligned among the images, the absolute value addition is appropriate. In the case of DWI, the phases are not aligned due to physiological body motions such as blood flow and cerebrospinal fluid flow, and thus the absolute value addition is often used.

In general, noise included in the image exhibits a Gaussian distribution, but in the case of an absolute value image, in a region having a low SNR such as a background region of the image, the noise is close to a Rayleigh distribution and becomes non-Gaussian. Therefore, when a plurality of absolute value images are added, noise reduction effect cannot be sufficiently obtained.

Meanwhile, in the complex addition, no problem caused by the non-Gaussian of the noise exists, but in the case of the complex addition, it is necessary to execute processing of aligning the phases among a plurality of images to some extent, and a phase correction technique for the processing has been proposed. For example, Diffusion Tensor Imaging (DTI) With Retrospective Motion Correction for Large-Scale Pediatric Imaging, Samantha J. Holdsworth, JOURNAL OF MAGNETIC RESONANCE IMAGING 36:961-971 (2012) (hereinafter, referred to as Holdsworth) discloses that for each of a plurality of images, a global phase variation is corrected by a low-pass filter or the like, and then complex addition is executed. Holdsworth also reports how results of the complex addition are obtained when a filter size (smoothness degree) is varied, and a trade-off exists between occurrence of an artifact and the noise reduction effect in the filter size.

SUMMARY OF THE INVENTION

As described above, smoothing using the filter as described in Holdsworth has a trade-off problem that an artifact is likely to occur in a region in which a signal from a subject is present (referred to as a signal region) when a filter having a high noise reduction effect, that is, a high smoothness degree is used, and conversely, when a filter that prevents the occurrence of such an artifact is used, the noise reduction effect is reduced, and it is not possible to solve both.

An object of the invention is to propose a method capable of executing appropriate phase correction by a simple method in which occurrence of an artifact in a signal region is prevented and noise in a background region is reduced. It should be noted that in the present specification, a signal region indicates a region having a high SNR (for example, an SNR of 5 or more) and a background region indicates a region having a low SNR (for example, an SNR of 1 or less).

In the invention to solve the problem described above, two or more types of smoothing processing having different smoothing degrees are executed on a complex image (or an image having phase information of the complex image), and each of smoothed phase images thus obtained is added using a weight based on a signal value or the like of an intensity image to obtain a phase image for correction. As a result, for example, phase correction equivalent to phase correction in which a smoothing degree is weakened in the signal region and a smoothing degree is strengthened in the background region is realized, and a trade-off problem of one filter is solved.

That is, an MRI device according to the invention includes: an imaging unit configured to measure a nuclear magnetic resonance signal generated from a subject; and an image processing unit configured to generate an image of the subject using the nuclear magnetic resonance signal acquired by the imaging unit. The image processing unit includes a phase correction unit configured to execute phase correction for each of a plurality of complex images obtained by performing imaging a plurality of times, and a complex addition unit configured to add the plurality of complex images which have been subjected to the phase correction. The image processing unit further includes a smoothing unit configured to execute two or more types of smoothing processing with different smoothing degrees on the complex image or an image having phase information of the complex image, and a weighted addition unit configured to execute weighted addition on results obtained by the smoothing unit smoothing with different smoothing degrees. The phase correction unit is configured to execute phase correction on the complex image using a phase of a complex image obtained after the weighted addition by the weighted addition unit.

In addition, an image processing method according to the invention is an image processing method for processing a plurality of complex images obtained by performing imaging a plurality of times by a magnetic resonance imaging device, and executes processing including the following steps for each of the plurality of the complex images.

A smoothing step of executing two or more types of smoothing processing with different smoothing degrees; a step of calculating a weight based on a signal value of an intensity image of the complex image; a step of executing weighted addition, by using the weight, on images each obtained by the two or more types of smoothing processing; a step of correcting a phase of the complex image using an image obtained by the weighted addition; and a step of complexly adding the plurality of complex images whose phases are corrected.

The plurality of complex images are, for example, images obtained by diffusion weighted imaging.

According to the invention, by applying filters having different smoothness degrees to a complex image and executing weighted addition on the smoothing results with weights having a predetermined distribution, it is possible to obtain the same result as that obtained by processing with filters having different smoothness degrees depending on a region of an image.

For example, by executing the weighted addition using a weight calculated in accordance with a signal value of an intensity image, it is possible to obtain a phase image smoothed appropriately for each of regions having different signal-to-noise ratios (for example, a signal region and a background region). By complexly adding the complex images whose phases are corrected using the smoothed phase images, it is possible to obtain noise reduction effect while preventing the occurrence of the artifact in an image obtained by addition.

DESCRIPTION OF EMBODIMENTS

Hereinafter, embodiments of an MRI device according to the invention will be described with reference to the drawings.

Figure 1:
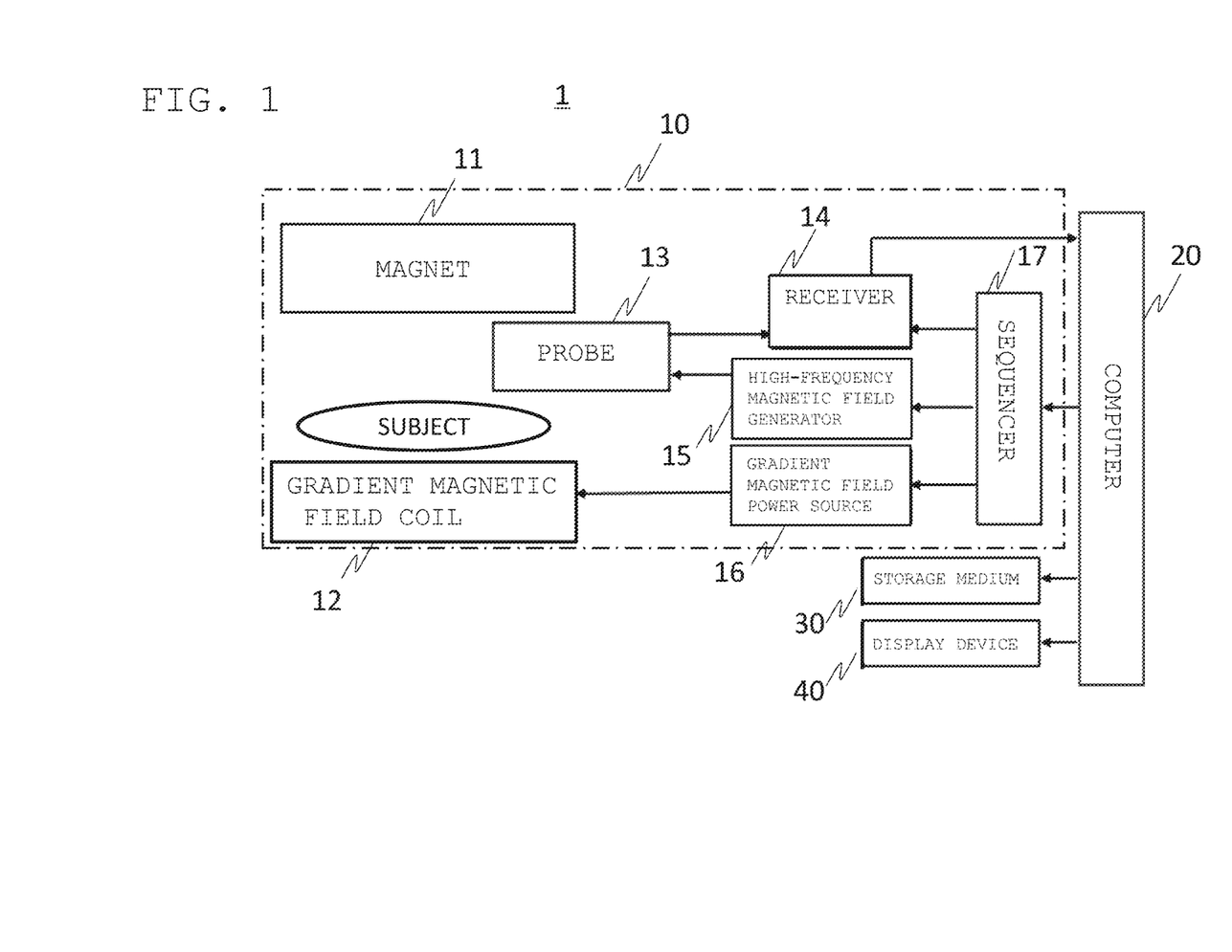
FIG. 1 is a diagram illustrating an overview of an MRI device to which the invention is applied.

First, a configuration of the MRI device to which the invention is applied will be described. As illustrated in FIG. 1, a configuration of an MRI device 1 is the same as a general MRI device. The MRI device includes a magnet 11 that generates a uniform static magnetic field in an inspection space in which a subject is placed, a gradient magnetic field coil 12 that gives a magnetic field gradient to the static magnetic field generated by the magnet 11, a probe 13 that includes a transmitting coil for applying a pulsed high-frequency magnetic field to the subject to cause nuclear magnetic resonance in nuclei of atoms constituting tissue of the subject and a receiving coil for receiving a nuclear magnetic resonance signal generated from the subject, a receiver 14 connected to the receiving coil, a high-frequency magnetic field generator 15 to which the transmitting coil is connected, a gradient magnetic field power source 16 to which the gradient magnetic field coil 12 is connected, a sequencer 17 that controls the receiver 14, the high-frequency magnetic field generator 15, and the gradient magnetic field power source 16 in accordance with a predetermined pulse sequence, and a computer 20. Among the elements described above, the elements other than the computer 20 are collectively referred to as an imaging unit 10.

The nuclear magnetic resonance signal received by the receiver 14 of the imaging unit 10 is digitized and transmitted to the computer 20 as measurement data.

A structure, a function, and the like of each unit that constitutes the imaging unit 10 are the same as those of known MRI devices, and the invention can be applied to various types of known MRI devices and elements, and thus detailed descriptions of the imaging unit 10 will be omitted here.

The computer 20 may be implemented by a computer or a workstation including a CPU or a GPU, and a memory, and has a function of controlling an operation of the imaging unit 10 and an image processing function of executing various calculations on the measurement data acquired by the imaging unit 10 or an image reconstructed based on the measurement data. Each function of the computer 20 is realized by, for example, uploading and executing a program of each function by the CPU or the like. Some of the functions of the computer 20 may be realized by hardware such as a programmable IC (ASIC or FPGA). Further, the functions of the computer 20 may be realized in a remote computer connected to the MRI device 1 wirelessly or by wire or a computer constructed on a cloud.

The computer 20 includes a storage device (storage medium 30) that stores data and results (including intermediate results) necessary for control and calculation, and a user interface (UI) unit 40 for displaying a GUI or a calculation result to a user and receiving a designation from the user. The UI unit 40 includes a display device and an input device (not shown).

The MRI device according to the present embodiment is characterized by processing in the computer 20, in particular, processing of a nuclear magnetic resonance signal acquired by the imaging unit 10 or an image (complex image) reconstructed based on the nuclear magnetic resonance signal. Specifically, the computer 20 includes a complex addition unit that adds a plurality of complex images obtained by imaging the same subject a plurality of times, and a phase correction unit that corrects a phase of each complex image to be added. The phase correction unit executes smoothing processing having different intensities, and executes phase correction of the complex image by executing weighted addition of processing results.

Figure 2:
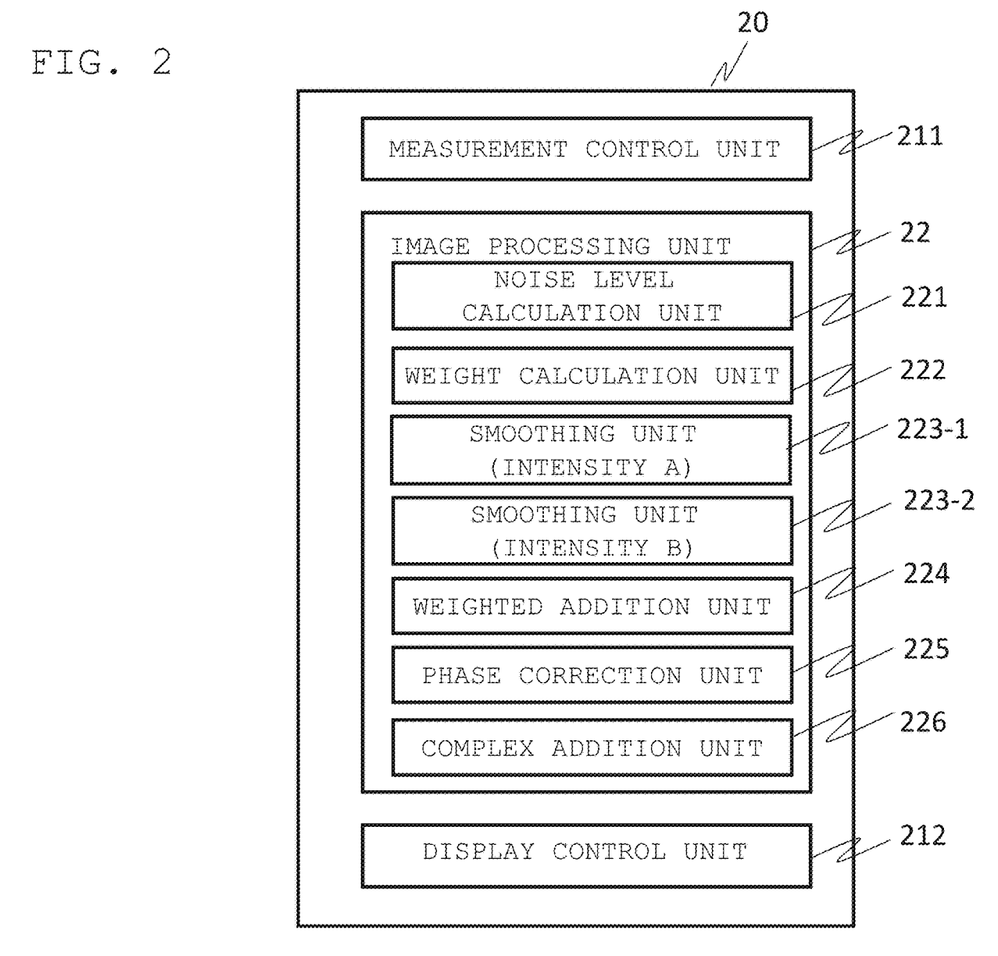
FIG. 2 is a functional block diagram of a computer provided in the MRI device of an embodiment.

FIG. 2 illustrates a configuration example of the computer 20 that implements the above functions. As illustrated in FIG. 2, the computer 20 includes a measurement control unit 211, a display control unit 212, and an image processing unit 22. The image processing unit 22 includes a noise level calculation unit 221, a weight calculation unit 222, smoothing units 223-1 and 223-2, a weighted addition unit 224, a phase correction unit 225, and a complex addition unit 226. Although not illustrated in FIG. 2, the image processing unit 22 includes a function for image reconstruction included in a computer of a normal MRI device, for example, a function of executing Fourier transform or inverse transform, a successive approximation calculation function, or the like. In addition, a necessary function may be added according to a mode of imaging, or a part of the functional units included in FIG. 2 may be omitted.

The measurement control unit 211 calculates a pulse sequence used in imaging based on a pulse sequence and an imaging condition (imaging parameter) which are set by a user or set in advance by an inspection protocol or the like, sets the pulse sequence used in imaging in the sequencer 17, and controls the operation of the imaging unit 10 via the sequencer 17.

The display control unit 212 controls to display an image obtained by image processing, the GUI for receiving a user designation, and the like on a display device provided in the UI unit 40.

The image processing unit 22 executes the image reconstruction using measurement data, phase correction of a reconstructed image (complex image), and complex addition of complex images subjected to the phase correction.

Hereinafter, an operation of the MRI device having the above configuration and processing of the image processing unit 22 will be described in detail.

Figure 3:
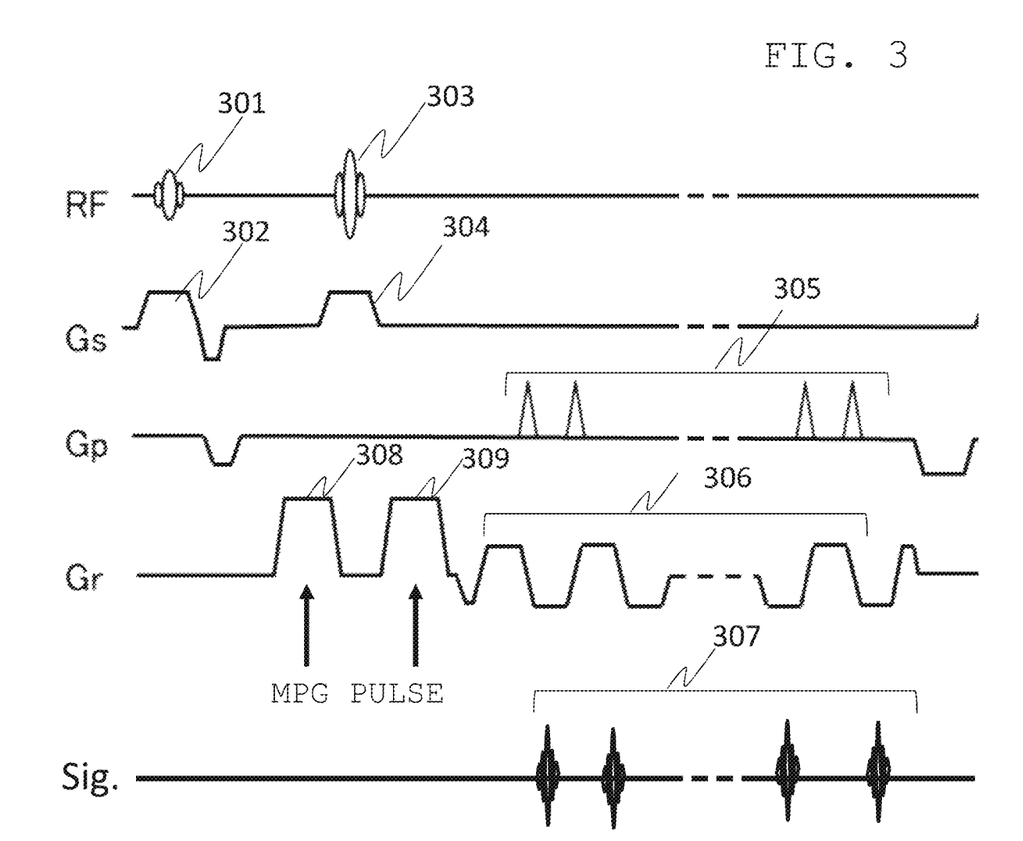
FIG. 3 is a diagram illustrating an example of a DWI sequence executed by an imaging unit.

When imaging is started under the control of the measurement control unit 211, the MRI device 1 executes the imaging in accordance with the pulse sequence set in the sequencer 17. Here, as an example, it is assumed that imaging (DWI) is executed using a DWI pulse sequence in which the effect of the phase correction described above is remarkably obtained. An example of a typical DWI pulse sequence is illustrated in FIG. 3. In FIG. 3, RF and Sig. respectively indicate an application timing of a high-frequency magnetic field pulse (RF pulse) and an echo signal acquisition timing, and Gs, Gp, and Gr respectively indicate an application timing of a gradient magnetic field pulse in a slice direction, a phase encoding direction, and a readout direction.

The DWI pulse sequence illustrated in FIG. 3 is a spin echo type EPI sequence, and after an excitation RF pulse 301 and an inversion RF pulse 303 are applied together with slice selection gradient magnetic fields 302 and 304, a blip-shaped phase encoding gradient magnetic field pulse 305 is applied, and a readout gradient magnetic field pulse 306 is applied while a polarity thereof being inverted, and thus an echo signal 307 is generated. In the DWI, by further applying a pair of MPG pulses 308 and 309 having high intensity before and after the application of the inversion RF pulse 303, a phase of a static spin largely changed in the MPG pulse 308 is returned in the MPG pulse 309, whereas a phase of a moving spin is largely changed according to a direction of movement. Therefore, in a region where water molecules are diffused in a random direction, since the phase varies, the signal decreases, and it is possible to obtain a high-contrast image in which a difference between a tissue with small diffusion and a tissue with large diffusion is large.

In FIG. 3, a case where an application axis of the MPG pulse is the readout direction Gr is illustrated as an example. The application axis of the MPG pulse may be any one of three axes (Gs, Gp, Gr) or a combination thereof. In addition, FIG. 3 illustrated a two-dimensional sequence in which phase encoding is executed on one axis. Alternatively, a three-dimensional sequence in which the phase encoding is added to the Gs axis may also be used.

The echo signal 307 collected by the execution of the DWI sequence described above is received by the receiver 14 and then transmitted to the computer 20 as digitized measurement data.

The sequencer 17 repeats the pulse sequence described above and collects a plurality of pieces of measurement data (k-space data) including a number of echo signals required for one image for the same subject. That is, a plurality of pieces of image data is collected by imaging a plurality of times. The computer 20 adds the plurality of pieces of image data to reconstruct one image.

Next, an embodiment of the image reconstruction in the computer 20 (processing of the image processing unit 22) will be described.

First Embodiment

The processing of the present embodiment will be described with reference to FIG. 4.

Figure 7:
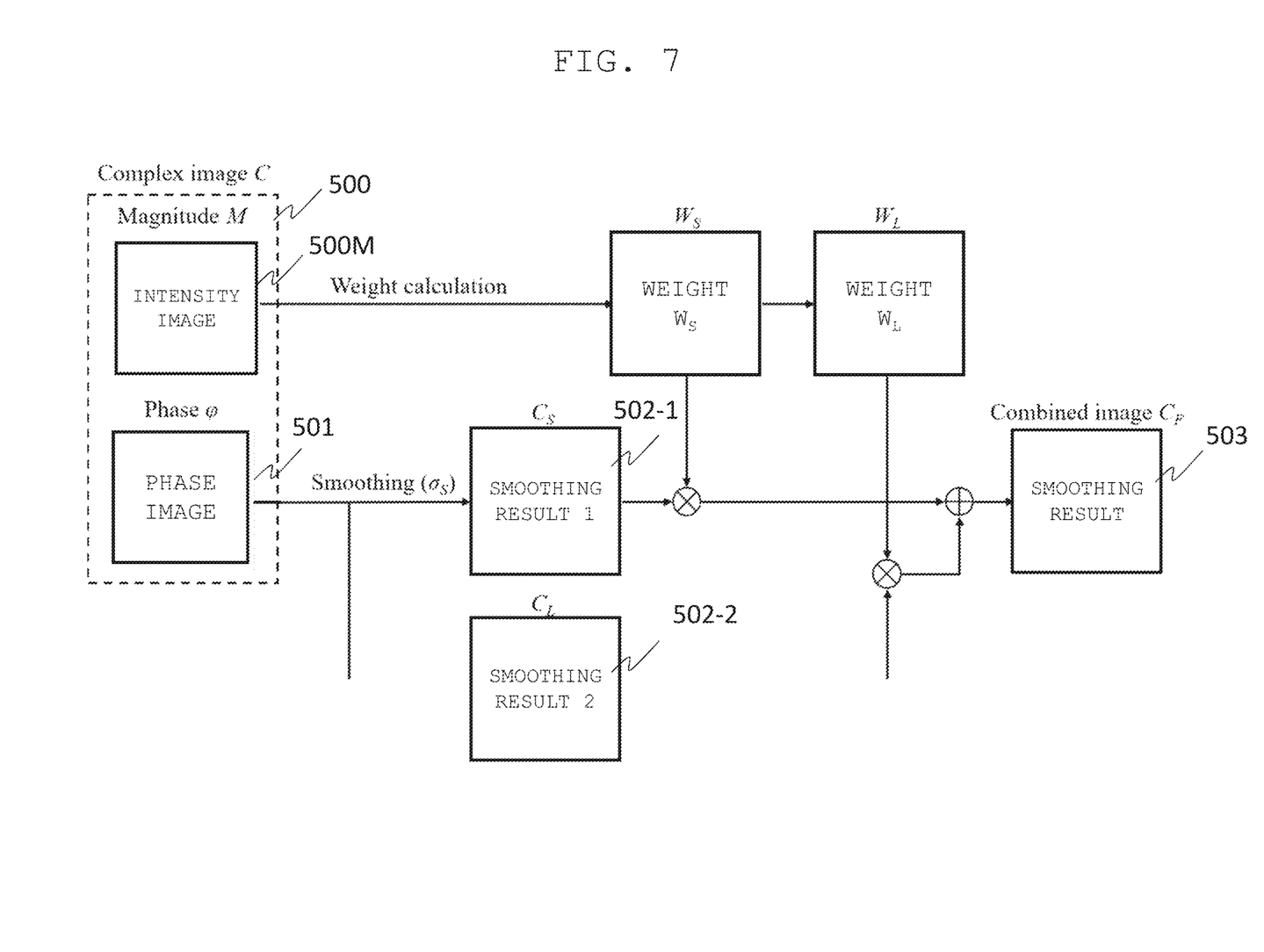
FIG. 7 is a diagram illustrating processing of a smoothing unit and a weighted addition unit according to the embodiment.

First, the image processing unit 22 converts the measurement data (k-space data) obtained for each time of imaging into image data by executing inverse Fourier transform (S401). Accordingly, one image is obtained for each time of imaging. The image is a complex image having intensity information and phase information. That is, as illustrated in FIG. 7, a complex image 500 includes an intensity image 500M and a phase image 501.

The image processing unit 22 executes the complex addition of the plurality of complex images to obtain one image (S407), and executes the phase correction of each complex image (phase image) before the complex addition. As illustrated in FIG. 5, in the phase correction, an uncorrected complex image (or phase image) 501 is smoothed to correct global phase variation. By obtaining a phase difference between a smoothed complex image (or phase image) 503 and the uncorrected complex image 501, a corrected complex image (phase-corrected image) in which global phase variation is corrected is obtained as a difference image 505. For example, the corrected complex image 505 can be obtained by the following complex division.

$$C_{corr}(x,y)=C(x,y)/\exp(i\cdot\varphi_F(x,y)) \quad (1)$$

Here, $C_{corr}(x, y)$ represents a corrected complex image, $C(x, y)$ represents an uncorrected complex image, and $\varphi_F(x, y)$ represents a smoothed phase image.

In the smoothing, in the present embodiment, processing with different degrees of smoothing is executed, and the smoothed phase image is subjected to weighted addition to obtain a smoothed phase image 502.

It should be noted that the smoothing can take some methods such as a method of directly smoothing a complex image including phase information and intensity information, a method of extracting a phase component from a complex image and smoothing the complex image including only the phase component, and a method of creating a phase image from a complex image and smoothing the phase image. A result obtained by the weighted addition is obtained by smoothing a phase of an original complex image. However, processing until the resultant image or the phase image 502 used for the phase correction described above is obtained is different depending on the method. Details of the method will be described later, and in the present embodiment, a case where the complex image or the complex image including only the phase component is smoothed will be described as an example.

Weights for the results obtained by the smoothing having different intensities are weights having a distribution corresponding to the intensity image, and differ in weights multiplied by the plurality of smoothing results depending on a position of the image. A criterion for calculating the weight is not limited, and the weight can be calculated based on, for example, the signal value (signal-to-noise ratio) of the intensity image. For example, a weight of a smoothed image having a high smoothing degree is larger in the background region than in a region where a signal from the subject is present (signal region), and conversely, a weight of a smoothed image having a small smoothing degree is smaller in the background region than in the region where the signal from the subject is present (signal region).

Therefore, first, the noise level calculation unit 221 calculates an SNR (distribution) of the image. The SNR can be expressed by Equation (2) where an intensity distribution (pixel value) of the intensity image (absolute value image) is M and a noise level is η (S402).

$$SNR(x,y) = M(x,y)/\eta \quad (2)$$

In Equation (2), x and y represent a position of a pixel.

The noise level η may be calculated by any of various methods such as a method of calculating based on a standard deviation of the pixel values, a method of calculating based on an average value or a variance of the pixel values after removing an edge of the image, and a method of obtaining based on a standard deviation of the background region (for example, four corners) of the image. In the present embodiment, it is provided that a spatial noise amount is uniform, but a spatial distribution of noise may be assumed based on information such as a G factor calculated by parallel imaging reconstruction. For the intensity image M(x, y), an intensity image smoothed by a median filter or the like may be used in order to reduce influence of noise in a weighted image. Alternatively, in order to shorten a calculation time, an intensity component of the complex image subjected to weak smoothing executed by the smoothing unit may be used as it is.

Figure 6:
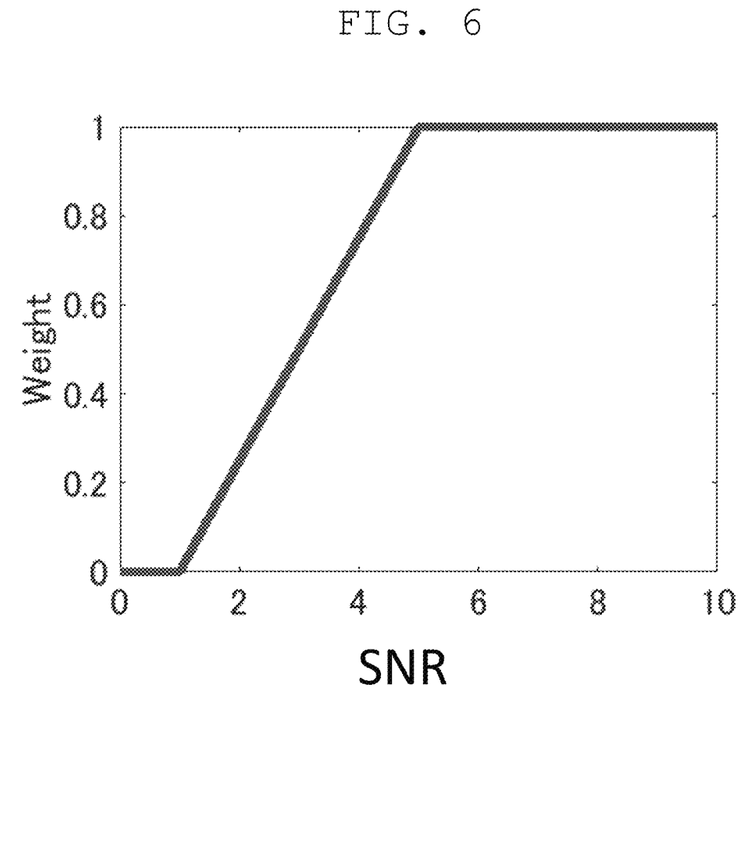
FIG. 6 is a diagram illustrating an example of a weight.

Next, the weight calculation unit 222 calculates, using the SNR calculated by the noise level calculation unit 221, weights $W_S$ and $W_L$ to be used when phase images (smoothed phases) smoothed by the two smoothing units 223-1 and 223-2, which will be described later, are subjected to the weighted addition (S403). The weight is not particularly limited as long as the weight monotonically increases (monotonically decreases) with respect to a change in the SNR. For example, as illustrated in FIG. 6, a function may be used in which the weight is set to zero for a pixel having an SNR equal to or lower than a lower threshold t1 and the weight is set to one for a pixel having an SNR equal to or higher than an upper threshold t2.

For example, the $W_S$ can be calculated by the following Equation (3).

$$W_s = \begin{cases} 0 & (SNR \le t_1) \\ \frac{SNR - t_1}{t_2 - t_1} & (t_1 < SNR \le t_2) \\ 1 & (SNR > t_2) \end{cases} \quad (3)$$

On the contrary, $W_L$ is calculated using a function ($W_L = 1 - W_S$) in which the weight is set to one for a pixel having an SNR equal to or lower than t1 and the weight is set to zero for a pixel having an SNR equal to or higher than t2. The thresholds t1 and t2 that define the start and end of raising are not limited, but may be, for example, set as follows.

$$t1=1 \text{ and } t2=5$$

By setting these values, it is possible to distinguish the background region in which non-Gaussian of a noise distribution is increased and substantially is a Rayleigh distribution and the signal region in which the noise distribution is substantially the Gaussian distribution by weighting. The threshold may be set by default, or may be set by receiving a user setting or a user adjustment via the GUI which will be described later.

On the other hand, the smoothing units 223-1 and 223-2 smooth the complex image or the phase image 501 using filters having different smoothing intensities (S404). As for the phase image 501, a phase component Cφ is extracted by dividing a complex image C to be processed by an absolute value image |C| of the complex image C (Cφ)=C/|C|), and a complex image having only this phase component can be used as the phase image 501. The smoothing may be executed on the complex image C. When only the phase component is extracted, it is advantageous in that information of the absolute value is not mixed, and when the complex image is used as it is, it is advantageous in that the information of the absolute value is stored. It may be selected as appropriate in accordance with a target site, a disease to be diagnosed, or the like.

As the filter, known smoothing filters such as a Gaussian filter and a low-pass filter may be used. In addition, for example, when a Gaussian filter is applied to the complex image, it is possible to calculate a smoothed complex image by implementing a convolution operation on a Gaussian kernel having an appropriate kernel size for each of a real number component (real image) and an imaginary number component (real image) of the complex image. The smoothing intensity can be increased or decreased by varying a kernel size (also referred to as a filter size) of a filter function to be used. The smoothing intensity can be increased by increasing the kernel size, and can be decreased by decreasing the kernel size.

It should be noted that in the present specification, parameters for varying the smoothing intensity are collectively referred to as the kernel size. For example, when the image is smoothed by regularization processing, a regularization parameter corresponds to the kernel size in the present specification. In the present specification, the smoothing intensity is defined to increase as the kernel size increases. However, in general, a relation between the kernel size and the smoothing intensity is changed depending on the smoothing method and the kernel size, and is not limited to this definition.

The kernel size may be set by default, or may be set by receiving the user setting via the GUI in the same manner as the threshold for the weight. When the smoothing intensity is set in advance, an appropriate value can be set based on, for example, a relation with the noise reduction effect in the background region, a relation with an artifact occurrence amount in the signal region, and the like. Specifically, for a filter having a high intensity, the noise reduction effect in the background region increases as the filter size increases, and when the filter size is equal to or larger than a certain size, the noise level becomes a constant value; therefore, the filter size can be set to the minimum value in a range where the noise level is the constant value. In contrast, for a filter having a low intensity, a maximum filter size that does not cause artifacts in the signal region can be set as the filter size with low intensity. The invention is not limited to these methods, and the filter size may be set by default on the basis of an empirically predictable noise level, or may be adjusted by the user.

Next, the weighted addition unit 224 executes the weighted addition of the smoothed phases processed by the two smoothing units 223-1 and 223-2 using the weights $W_S$, and $W_L$ calculated by the weight calculation unit 222 (S405). Specifically, as illustrated in FIG. 7, a phase 502-1 smoothed by the smoothing unit 223-1 using a filter having a small intensity (filter size $\sigma_S$) is multiplied by the weight $W_S$ and a phase 502-2 smoothed by the smoothing unit 223-2 using a filter having a large intensity (filter size $\sigma_L$) is multiplied by the weight $W_L$, and these phases are added to obtain a smoothed phase 503. It should be noted that the "phases" 502-1, 502-2, and 503 described above mean the results of smoothing, and are phase images including only phase components in this case, but when the smoothing processing is executed on the complex image itself, the complex image is read as a smoothed complex image.

As described above, by executing the weighted addition on two smoothing results (smoothed phase images), in the region having a high SNR, that is, the signal region, smoothing having a low intensity is executed without impairing the signal value, and in the region having a low SNR, that is, the background region, smoothing having a high noise reduction effect is executed.

As illustrated in FIG. 5, the phase correction unit 225 obtains a difference between a phase of an original complex image (phase image) 501 and the smoothed phase 503 to obtain a corrected phase 505 (S406). At this time, when the complex image is smoothed as it is, a complex image $C_F$ ($C_F=C_SW_S+C_LW_L$) after the weighted addition is converted to a phase image $\varphi_F$ by the following Equation (4) and is used as the smoothed phase 503.

$$\varphi_F = \arg(C_F) \quad (4)$$

As described above, the difference between the original phase image 501 and the smoothed phase image 503 is obtained by complex division using Equation (1).

After the above processing S402 to S406 is executed on all complex images to be added, the complex addition unit 226 replaces the phase images 501 of the complex images 500 before processing with the corrected phases 505, and executes the complex addition together with the intensity images 500A (the following Equation (5)) to obtain one added image $X_{cmp}$(S407).

$$X_{cmp} = \frac{1}{n}\sum_{i=1}^{n} C_{corr}^i \quad (5)$$

In Equation (5), $C_{corr}^i$ represents individual (i-th) complex images constituting n corrected complex images.

The obtained added image is converted into an intensity image and a phase image, and then the intensity image and the phase image are displayed on the display device of the UI unit 40 by the display control unit 212, and are stored in a storage device 30 as necessary.

In the added image obtained by the above processing, since noise is effectively reduced without excessive phase correction of the signal region, the occurrence of artifacts is prevented and the noise is reduced.

According to the MRI device of the present embodiment, when a plurality of complex images are complexly added, as processing of correcting a phase of each complex image, a plurality of smoothing results obtained by executing smoothing having different smoothing intensities are weighted according to noise characteristics that are different depending on regions and added, thereby obtaining a result similar to that obtained by executing the smoothing processing according to the noise characteristics, and noise reduction and artifact prevention, which are trade-off in smoothing processing of the related art, can be simultaneously achieved.

In particular, in complex addition of DWI, which is important to improve SNR, accurate phase correction can be executed on each complex image to be added, and a DWI image useful for diagnosis can be provided.

In addition, according to the MRI device of the present embodiment, the above problem can be solved by a simple configuration in which two smoothing units are provided and smoothed phases are subjected to weighted addition. The present method is particularly effective for a region having a large phase variation caused by physiological body motion, such as a head region affected by cerebrospinal fluid motion, or an abdomen region affected by respiratory movement.

Figures 8A, 8B:
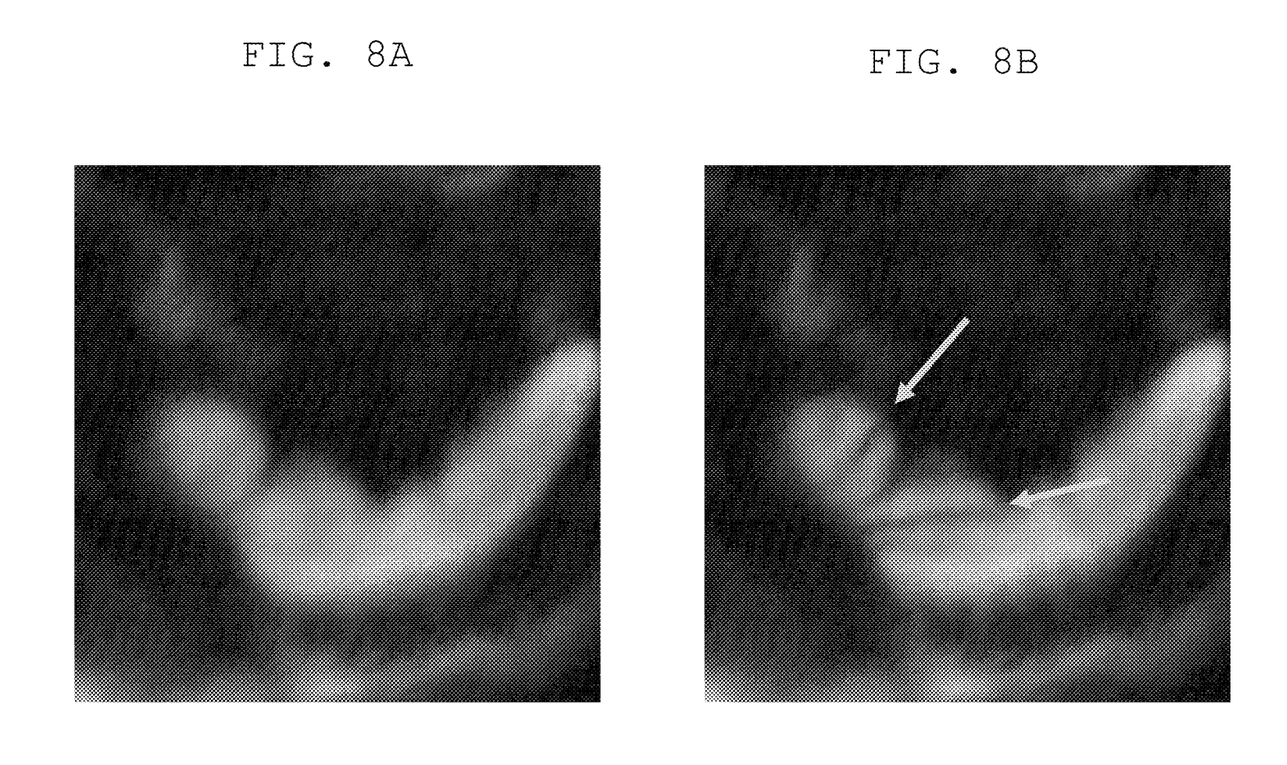
FIGS. 8A and 8B are diagrams illustrating an effect of the processing by the image processing unit according to the embodiment.

FIG. 8A illustrates an image (A) obtained by executing the phase correction of the present embodiment and complex addition, and FIG. 8B illustrates an image (B) obtained by executing complex addition according to a related-art method. In the related-art method, smoothing by one filter size, phase correction, and complex addition are executed, and in this example, a filter having a kernel size capable of sufficiently reducing noise of a background signal is used.

In an image obtained by the related-art method, in a region where physiological body motion is large, that is, a region where spatial phase change is large, the phase correction is insufficient and phases are not aligned between imaging. Therefore, an artifact such as a signal loss occurs in an added image, as indicated by an arrow in (B).

In contrast, in the image (A) subjected to the complex addition after the phase correction by the method of the invention, an adaptive kernel size is set according to the SNR, and the signal region is corrected with a phase subjected to weak smoothing and the background region is corrected with a phase subjected to strong smoothing, and thus it is possible to sufficiently reduce noise in the background region while aligning the phases of the signal region between the imaging (left figure).

Modification of First Embodiment

Although the configuration and operation of the MRI device according to the embodiment are described above, the invention is not limited to the above-described embodiment, and various modifications such as changing an imaging method as a target, replacing the above-described elements with another element, and adding a new element can be made.

For example, in the first embodiment, a case where a complex image itself or a complex image including only a phase component extracted from the complex image is used as a smoothing target has been described. Alternatively, a phase image may be generated from the complex image and smoothing processing and weighted addition may be executed on the phase image.

In this case, first, arg of the complex image C is obtained in the same manner as in Equation (4), and the phase image $\varphi$ is created. The created phase image is subjected to phase unwrapping, and then is smoothed. The smoothing of the phase image may be executed by using a filter similar to the smoothing of the complex image. Fourier transform may be executed on the phase image, and only a low frequency band of data after the Fourier transform may be extracted and inverse Fourier transform may be executed. By varying a size of the extracted low frequency band region, a smoothing degree can be varied.

Thereafter, weighted addition of the smoothed phase image is executed in the same manner as in the first embodiment. In this modification, unwrapping, which is unnecessary in the first embodiment, is required. However, since the phase image subjected to the unwrapping can be processed as real numbers, an advantage is present that various existing smoothing methods (regularization processing and the like) can be easily applied.

As another modification, for example, the embodiment described above shows a case where the smoothing unit includes two types of smoothing units, that is, a smoothing unit having a high smoothing degree and a smoothing unit having a low smoothing degree. Alternatively, a smoothing unit having an intermediate smoothing degree may be further added, and these weights may be set according to the signal (SNR) of the intensity image. In addition, in the embodiment described above, a case where the imaging method is DWI is described. It is noted that the invention can be applied to a case where complex addition of a plurality of images is executed regardless of the imaging method.

Second Embodiment

The present embodiment is an embodiment of a GUI for receiving user designation with respect to processing in the image processing unit 22, in particular, processing in the weight calculation unit 222 and the smoothing units 223-1 and 223-2. Other configurations are the same as those of the first embodiment, and redundant descriptions will be omitted.

Figure 9A:
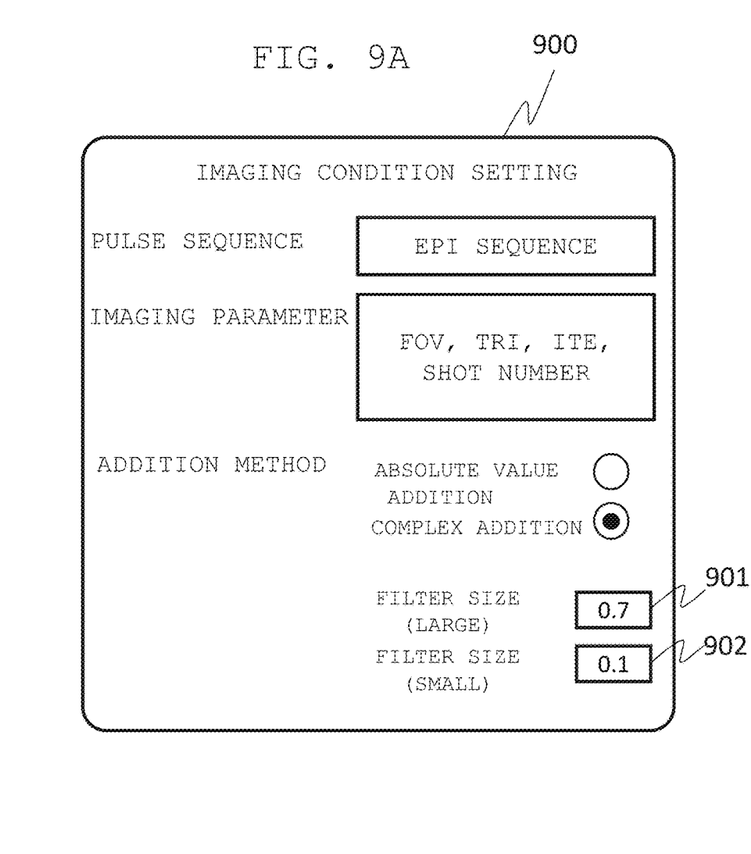
FIGS. 9A and 9B are diagrams illustrating an example of a GUI displayed on a display device.
Figure 9B:
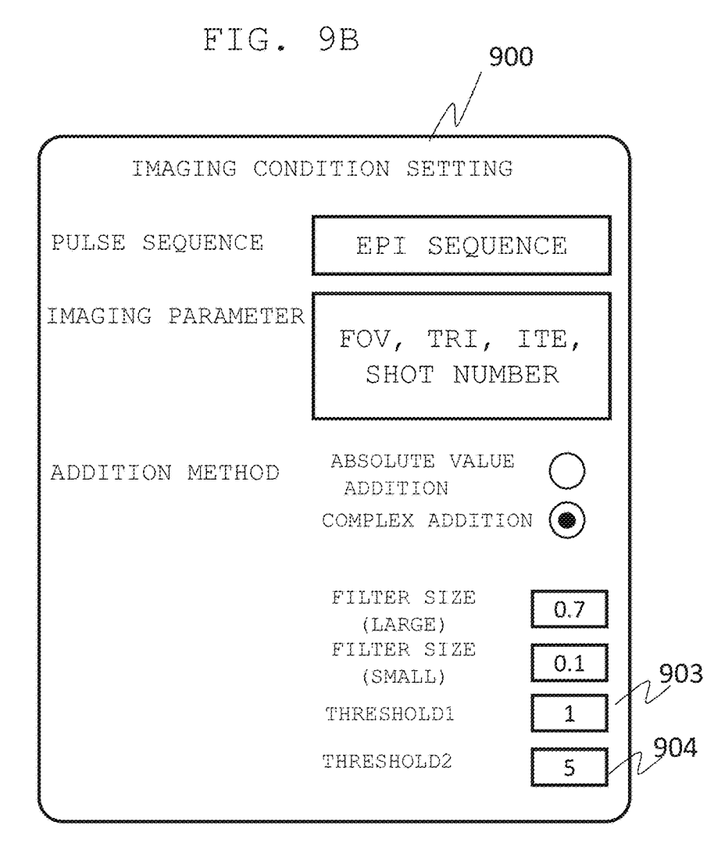

FIGS. 9A and 9B illustrate examples of GUIs displayed on the display device of the UI unit 40 by the display control unit 212. The examples illustrated in FIGS. 9A and 9B are both GUIs for setting a method of adding images (complex addition or absolute value addition) and a phase smoothing condition in the case of complex addition on an imaging condition setting screen 900. FIG. 9A is an example in which boxes 901 and 902 are provided for receiving filter sizes to be used by the smoothing units 223-1 and 223-2 when the complex addition is selected. FIG. 9B is an example in which boxes 903 and 904 are further provided for receiving thresholds for a weight function to be calculated by the weight calculation unit 222. In these boxes, values set as initial values may be displayed. In the examples illustrated in FIGS. 9A and 9B, numerical values are input to the boxes, but the display mode is not limited to that shown in FIGS. 9A and 9B. For example, a pull-down menu type GUI in which a menu is displayed when the complex addition is selected is used.

The user checks, for example, whether it is necessary to further reduce background noise, whether artifacts are sufficiently prevented, or the like from an image (an image after complex addition) displayed on the display device. The user performs adjustment such as changing a value of a filter size (large) to a larger value when the noise is required to be reduced, and reducing a filter size (small) or reducing a value of a threshold (for example, threshold 2) of the GUI of FIG. 9B when the artifacts are not sufficiently prevented.

Figure 4:
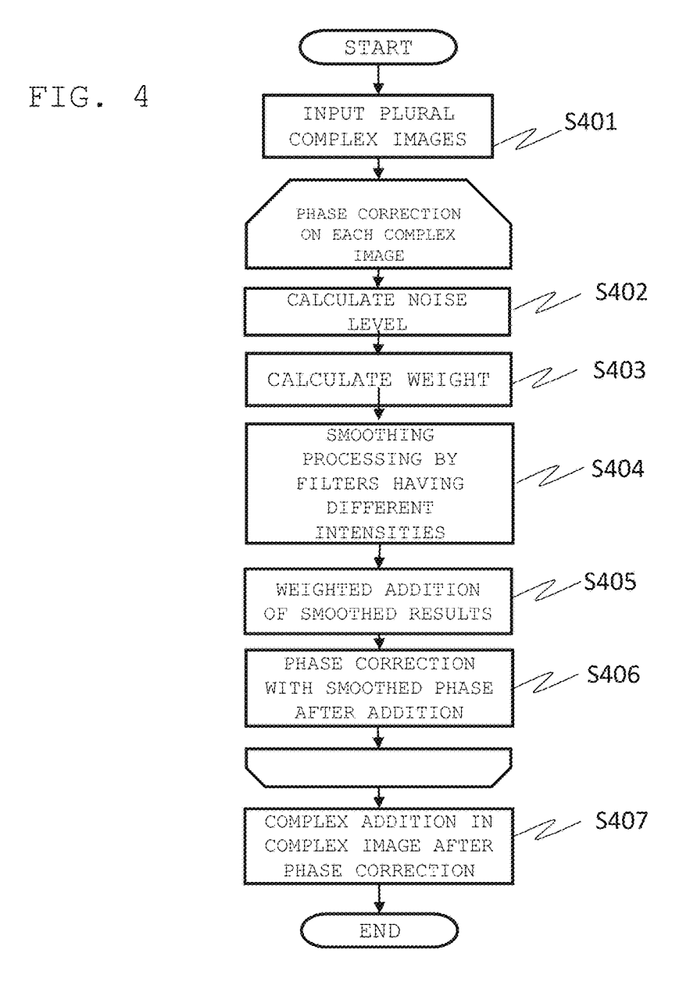
FIG. 4 is a flowchart illustrating processing of an image processing unit according to a first embodiment.
Figure 5:
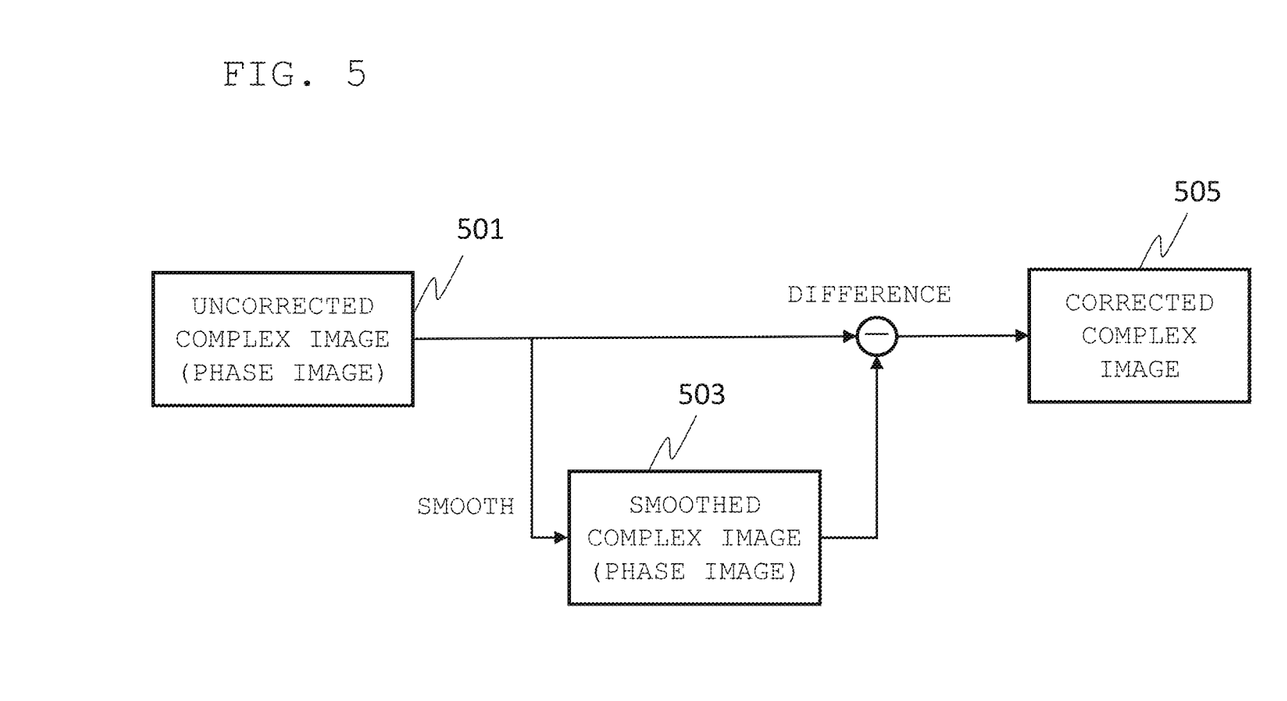
FIG. 5 is a diagram illustrating processing of a phase correction unit according to the embodiment.

The image processing unit 22 changes the filter sizes and the new thresholds for the weight received via the GUI, and executes the processing S402 to S407 illustrated in FIG. 4. Processing contents are the same as those in the first embodiment.

When the image processing unit 22 includes more than two types of smoothing units 223 having different smoothing degrees, the user may select one of the smoothing units 223, and a box or the like for selecting the smoothing units 223 may be displayed as a GUI.

According to the present embodiment, it is possible for the user to obtain an image more useful for diagnosis while checking the image.

Third Embodiment

In the embodiment described above, the case where the image processing unit 22 of the MRI device 1 executes processing such as the complex addition and the phase correction is described, but it is also possible to execute all or a part of the processing executed by the image processing unit 22 in an image processing device 2 independent of the MRI device 1. As a result, it is possible to reduce a calculation load of the image processing unit 22 of the MRI device 1. In addition, it is possible to execute post image processing at a place different from the MRI device 1.

Figure 10:
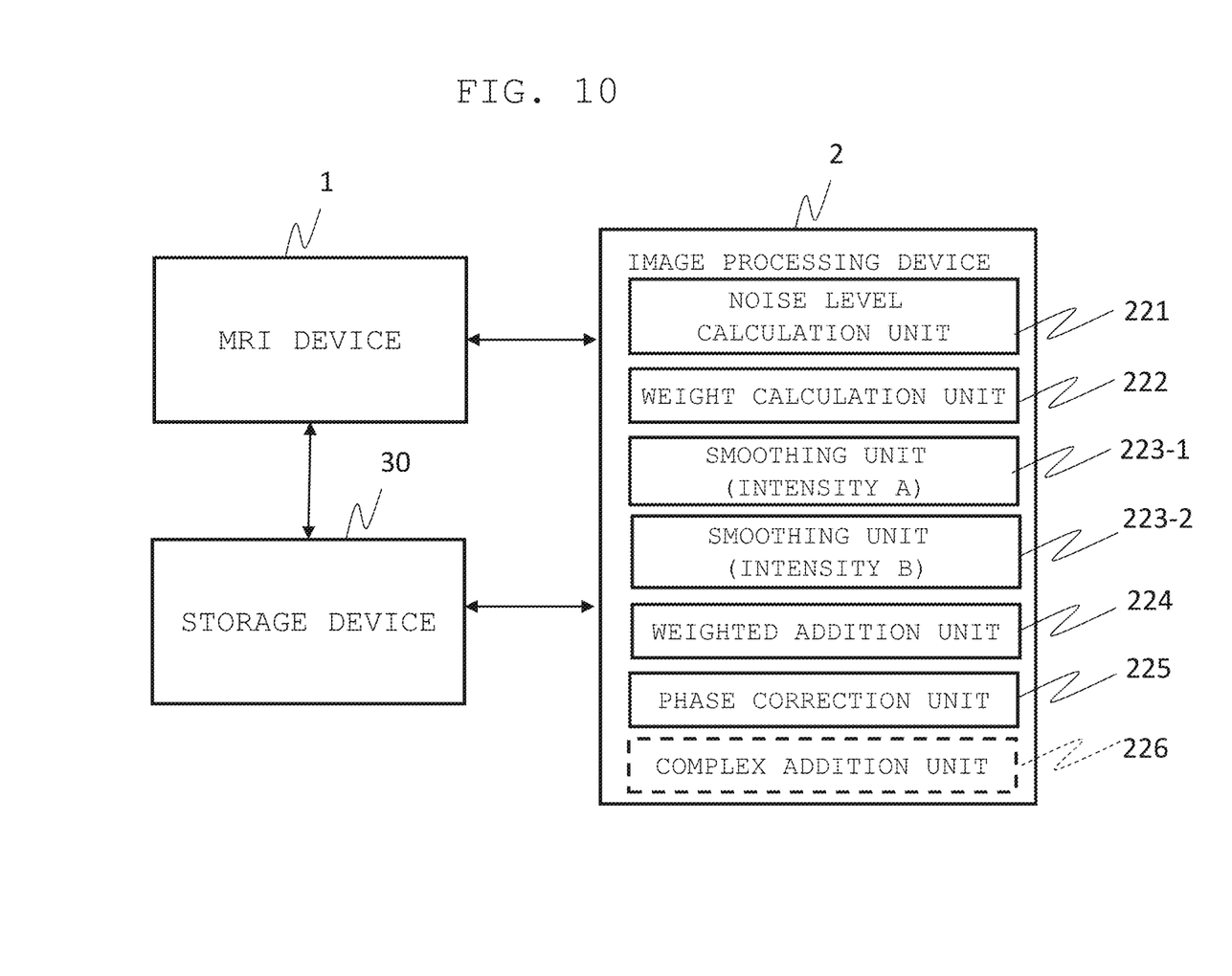
FIG. 10 is a configuration diagram illustrating an embodiment of an image processing device of the invention.

FIG. 10 illustrates a configuration example of the image processing device 2. The image processing device 2 is a device capable of transmitting and receiving data to and from the MRI device 1 by known communication units, a storage medium, or the like, and has a function of executing predetermined phase correction processing on a plurality of complex images received from the MRI device 1.

In order to implement the function, the image processing device 2 includes the same functional units as the image processing unit 22 of the computer 20 of the MRI device 1 illustrated in FIG. 2, that is, the noise level calculation unit 221, the weight calculation unit 222, the smoothing units 223-1 and 223-2, the weighted addition unit 224, the phase correction unit 225, and the complex addition unit 226. These functional units are the same as those of the image processing unit 22 of the MRI device 1 described above, and redundant descriptions will be omitted. The image processing device 2 may also be provided with a UI unit to receive a user instruction regarding the filter size and thresholds for the weight as described in the second embodiment.

FIG. 10 illustrates the case where the functions of the image processing device 2 are the same as the functions of the image processing unit 22 of the MRI device, but a part of the processing of the image processing unit 22, for example, only the functions of the smoothing unit and the weighted addition unit may be executed by the image processing device 2, results may be returned to the MRI device, and the phase correction and the complex addition may be executed in the MRI device.

What is claimed is:
1. A magnetic resonance imaging device, comprising:
an imaging unit configured to measure a nuclear magnetic resonance signal generated from a subject; and
an image processing unit configured to generate an image of the subject using the nuclear magnetic resonance signal acquired by the imaging unit, wherein
the image processing unit includes:
a phase correction unit configured to execute phase correction for each of a plurality of complex images obtained by performing imaging a plurality of times;
a complex addition unit configured to add the plurality of complex images obtained after the phase correction;
a smoothing unit configured to execute two or more types of smoothing processing with different smoothing degrees on the complex image or an image having phase information of the complex image; and
a weighted addition unit configured to execute weighted addition on results obtained by the smoothing unit smoothing with different smoothing degrees, and
the phase correction unit is configured to execute phase correction on the complex image using a phase of a complex image obtained after the weighted addition by the weighted addition unit.

2. The magnetic resonance imaging device according to claim 1, further comprising:
a weight calculation unit configured to calculate a weight of the weighted addition based on intensity information of the complex image.

3. The magnetic resonance imaging device according to claim 2, wherein
the image processing unit further includes a noise level calculation unit configured to calculate a signal-to-noise ratio based on the intensity information of the complex image, and
the weight calculation unit is configured to calculate the weight based on the signal-to-noise ratio.

4. The magnetic resonance imaging device according to claim 3, wherein
the weight calculation unit is configured to calculate, as a weight for a processing result having a high smoothing degree in the smoothing unit, a weight that is large for a region having a relatively low signal-to-noise ratio and is small for a region having a relatively high signal-to-noise ratio.

5. The magnetic resonance imaging device according to claim 2, wherein
the weight calculation unit is configured to calculate, as a weight for a processing result having a high smoothing degree in the smoothing unit, a weight such that a weight for a background region is one and a weight for a signal region in which a signal from a subject is present is zero.

6. The magnetic resonance imaging device according to claim 1, wherein
the smoothing unit is configured to execute smoothing on the complex image, and
the phase correction unit is configured to convert the complex image subjected to the weighted addition by the weighted addition unit into a phase image, and then to execute the phase correction of an uncorrected complex image using the phase image.

7. The magnetic resonance imaging device according to claim 6, wherein
the smoothing unit is configured to smooth a complex image including a phase component extracted from the complex image.

8. The magnetic resonance imaging device according to claim 1, wherein
the smoothing unit is configured to smooth a phase image created from the complex image, and
the phase correction unit is configured to execute the phase correction on an uncorrected complex image using a phase image obtained after the weighted addition by the weighted addition unit.

9. The magnetic resonance imaging device according to claim 1, wherein
the smoothing unit is configured to execute the smoothing processing using one or a plurality of filters selected from a Gaussian filter, a low-pass filter, and regularization processing.

10. The magnetic resonance imaging device according to claim 9, wherein
two or more types of the filters used by the smoothing unit have different kernel sizes.

11. The magnetic resonance imaging device according to claim 1, wherein
the plurality of complex images are images acquired by diffusion weighted imaging.

12. The magnetic resonance imaging device according to claim 1, further comprising:
a display control unit configured to cause a display device to display a GUI for receiving a user designation regarding a smoothing degree of a filter to be used by the smoothing unit.

13. The magnetic resonance imaging device according to claim 1, further comprising:
a display control unit configured to cause a display device to display a GUI for receiving a user designation regarding a weight calculated by the weight calculation unit.

14. An image processing device that processes an image captured by a magnetic resonance imaging device, the image processing device comprising:
a smoothing unit configured to execute two or more types of smoothing processing with different smoothing degrees on a complex image or an image having phase information of the complex image;
a weighted addition unit configured to execute weighted addition on results obtained by the smoothing unit smoothing with different smoothing degrees;
a weight calculation unit configured to calculate a weight to be used by the weighted addition unit based on an intensity image of the complex image; and
a phase correction unit configured to execute phase correction on the complex image using a phase of a complex image after the weighted addition by the weighted addition unit.

15. The image processing device according to claim 14, further comprising:
a complex addition unit configured to execute complex addition on a plurality of complex images, wherein
the complex addition unit is configured to add the plurality of complex images obtained after subjected to the phase correction by the phase correction unit.

16. An image processing method for processing a plurality of complex images obtained by performing imaging a plurality of times by a magnetic resonance imaging device, the image processing method comprising:
for each of the plurality of complex images,
a smoothing step of executing two or more types of smoothing processing with different smoothing degrees;
a step of calculating a weight based on a signal value of an intensity image of the complex image;
a step of executing weighted addition, by using the weight, on images each obtained by the two or more types of smoothing processing;
a step of correcting a phase of the complex image using an image obtained by the weighted addition; and
a step of complexly adding the plurality of complex images whose phases are corrected.

17. The image processing method according to claim 16, wherein
the plurality of complex images are images acquired by diffusion weighted imaging.

* * * * *